United States Patent [19]

Kaufman

[11] Patent Number: 4,666,434
[45] Date of Patent: May 19, 1987

[54] CATHETER LOCATING DEVICE

[76] Inventor: Jerry M. Kaufman, 20 Old Queens Blvd., Englishtown, N.J. 07726

[21] Appl. No.: 692,990

[22] Filed: Jan. 22, 1985

Related U.S. Application Data

[63] Continuation-in-part of Ser. No. 544,249, Oct. 21, 1983.

[51] Int. Cl.⁴ ............................................. A61M 5/32
[52] U.S. Cl. .................................... 604/179; 604/174; 128/DIG. 26
[58] Field of Search .......... 128/DIG. 26, 135, 207.17; 604/174–180, 4–6, 29, 93, 94

[56] References Cited

U.S. PATENT DOCUMENTS

| | | | |
|---|---|---|---|
| 3,017,887 | 1/1962 | Heyer | 604/178 |
| 3,626,938 | 12/1971 | Versaci | 604/179 |
| 3,939,832 | 2/1976 | Miller | 604/179 |
| 3,957,048 | 5/1976 | Jacobs | 604/180 |
| 4,108,174 | 8/1978 | Slivenko | 604/175 |
| 4,170,993 | 10/1979 | Alvarez | 604/180 |
| 4,332,248 | 6/1982 | DeVitis | 128/DIG. 26 |
| 4,585,443 | 4/1986 | Kaufman | 604/179 |

FOREIGN PATENT DOCUMENTS 0488991 12/1952 Canada .................................. 604/179

Primary Examiner—C. Fred Rosenbaum
Assistant Examiner—Mario Costantino
Attorney, Agent, or Firm—Lerner, David, Littenberg, Krumholz & Mentlik

[57] ABSTRACT

A device for securing catheters to grafts and the like implanted in patients, primarily for use in connection with dialysis treatments is disclosed, including an anchoring bracelet for attachment to the patient at a predetermined location at which the graft is located, a rotatable saddle rotatably mounted on the anchoring bracelet, in which the saddle includes an aperture adapted to receive the catheter, a contact surface having a shape adapted to mate with the graft, and a saddle channel extending between the aperture and the contact surface, and stabilizing tabs for preventing removal of the rotatable saddle from the anchoring bracelet so that the catheter can be accurately located in the graft and firmly anchored on the patient.

40 Claims, 6 Drawing Figures

CATHETER LOCATING DEVICE

CROSS-REFERENCE TO RELATED APPLICATION

This application is a continuation-in-part of U.S. application Ser. No. 544,249, filed on Oct. 21, 1983.

FIELD OF THE INVENTION

The present invention is directed to devices for securing catheters to patients. More particularly, the present invention is directed to devices for securing catheters within body fluid-carrying conduits, such as pre-implanted grafts, and particularly those used in connection with dialysis treatments. Still more particularly the present invention is directed to devices for firmly and accurately securing catheters to such body grafts so as to facilitate the constant dialysis techniques required for such patients.

BACKGROUND OF THE INVENTION

In the medical field the intravenous insertion of needles, catheters, cannulas and the like into a patient generally requires some means to secure the catheter or needle in place for the period of use. This has generally been done by positioning a gauze pad and/or by the application of strips of tape for securing the catheter and associated tubing to the patient so as to prevent any accidental removal of the catheter by sudden patient movement or the like. Obviously, the use of such a technique is not acceptable since the placement of the catheter is entirely non-uniform, or becomes a hit-or-miss proposition, proper placement of the catheter or needle is clearly not insured, such placement is quite slow, and is heavily dependent on the ability of the nurse or other technician who is applying the catheter, etc.

These problems become particularly acute in connection with the use of catheters in dialysis treatments, in which the patients generally require continual dialysis treatments and usually have a graft which has previously been implanted subcutaneously, and which requires continuing application and securing of the catheters during the entire dialysis procedure. Improper catheter application in such cases is thus not only painful, but this becomes a particularly harmful problem when the catheter misses or projects through the graft, thus invading the patient, with resultant problems of toxicity, etc. There has thus been a continuing search for new devices to replace the present ones, and to insure proper application and securing of the catheter or needle.

In particular, one such device is shown in U.S. Pat. No. 2,402,306 to Turkel. The device in this patent includes a support for the needle with extending leaf members which can be attached by tape or the like. The support includes means for angular entry of the needle, and in the embodiment shown in FIGS. 4, 5, 9, and 10 thereof there is provision for altering the angle of the needle. However, as in the other prior art devices, it still becomes necessary to try to carefully aim the catheter into the desired injection site, and no physical means are provided for insuring that the catheter is properly placed and aligned with a pre-implanted graft or the like.

A number of prior art devices have also been developed which incorporate some type of attempt to mate with a vein or other body fluid-carrying conduit. These include U.S. Pat. No. 4,332,248 to DeVitis, which has a guide with a V-shaped lower surface for such purposes, as well as U.S. Pat. No. 4,316,461 to Marais et al and U.S. Pat. No. 4,059,105 to Cutruzzula et al.

A number of other such devices have also been employed in an attempt to maintain the catheters in place after angular insertion. These include U.S. Pat. No. 3,900,026 to Wagner, which includes a protective device for covering the catheter, U.S. Pat. No. 3,288,137 to Lund, and U.S. Pat. No. 3,021,842 to Flood.

The search has therefore continued for a practical device which can accurately and securely assist in fixing the catheter in place, i.e., not only by permitting insertion at precisely the right location, angle, and depth, but which can also firmly secure the catheter in place without additional difficulty.

SUMMARY OF THE INVENTION

In accordance with the present invention it has now been discovered that these and other objects can be realized by the utilization of a device for securing a catheter to a body fluid-carrying conduit in a patient which includes anchoring means for attachment to the patient at a predetermined location at which the body fluid-carrying conduit is located, a rotatable saddle rotatably mounted on the anchoring means and including an aperture adapted to receive the catheter, a contact surface having a shape adapted to mate with the body fluid-carrying conduit in the patient, and a saddle channel extending between the aperture and the contact surface, and stabilizing means for preventing removal of the rotatable saddle from the anchoring means, so that the catheter can be accurately located in the body fluid-carrying conduit.

In one embodiment of the device of the present invention, the anchoring means includes a central aperture, and the rotatable saddle is rotatably mounted in that central aperture.

In accordance with one embodiment of the device of the present invention, the anchoring means includes a central portion and a pair of arm portions extending from opposite sides of the central portion, the arm portions being adapted to be affixed to the patient at the predetermined location. Preferably, the arm portions comprise flexible straps, and the device includes locking means for locking these flexible straps to the patient.

In accordance with another embodiment of the device of the present invention, the body fluid-carrying conduit comprises a pre-implanted graft forming a portion of the circulatory system of the patient.

In accordance with a preferred embodiment of the device of the present invention, the rotatable saddle and the anchoring means includes upper surfaces, and both these upper surfaces are in a common plane, and in addition the stabilizing means includes at least one stabilizing member mounted in a plane adjacent to that common plane and overlapping both of these upper surfaces, so as to retain the rotatable saddle in the central aperture. Preferably, a plurality of these stabilizing members are so utilized.

In a preferred embodiment of the device of the present invention, the at least one stabilizing member is mounted on the upper surface of the rotatable saddle, and preferably it has a substantially circular shape.

In accordance with another embodiment of the device of the present invention, the stabilizing means includes an outwardly extending circumferential flange on the rotatable saddle, and the central aperture includes a corresponding circumferential groove portion for retaining the flange portion when the rotatable saddle has been placed within the central aperture.

In accordance with another embodiment of the device of the present invention, the saddle channel includes a surface which is sufficiently hard so as to prevent penetration by the catheter. In a preferred embodiment, this surface is metallic.

In accordance with another embodiment of the device of the present invention, the aperture in the rotatable saddle includes stop means for limiting the depth to which the catheter may be inserted into the saddle channel. In a preferred embodiment, the stop means has a conical configuration which is adapted to mate with the shape of the catheter so as to stabilize the catheter after it has been inserted into the saddle channel.

In accordance with the catheter device of the present invention, there is provided a catheter including a needle member and tubular catheter conduit means for supplying fluid to or removing fluid from the needle member, anchoring means for attachment to the patient at a predetermined location at which a body fluid-carrying conduit is located, a rotatable saddle rotatably mounted on the anchoring means, the rotatable saddle including an aperture adapted to receive the catheter, a contact surface adapted to contact the body fluid-carrying conduit in the patient, and a saddle channel extending between the aperture and the contact surface, and stabilizing means for preventing removal of the rotatable saddle from the anchoring means, whereby the catheter can be accurately located in the body fluid-carrying conduit when it has been inserted into the aperture.

In accordance with one embodiment of the catheter device of the present invention, the anchoring means includes a central aperture, and the rotatable saddle is mounted in that central aperture.

In accordance with another embodiment of the catheter device of the present invention, the saddle channel in the rotatable saddle includes stop means for limiting the depth to which the catheter may be inserted into the saddle channel. In a preferred embodiment, the tubular catheter conduit means and the saddle channel in the rotatable saddle have corresponding shapes intended to mate with each other so that the catheter is stabilized after it has been inserted into the saddle channel. In a preferred embodiment, the corresponding shapes comprise corresponding conical surfaces.

In accordance with a preferred embodiment of the catheter device of the present invention, the rotatable saddle and the anchoring means include upper surfaces, both of which are disposed in a common plane, and the stabilizing means includes at least one stabilizing member mounted in a plane adjacent to that common plane and overlapping both the upper surfaces so as to retain the rotatable saddle in the central aperture. Preferably, a plurality of these stabilizing members are provided, and most preferably the at least one stabilizing member is mounted on the upper surface of the rotatable saddle. Preferably, the stabilizing member has a substantially circular shape.

In another embodiment of the catheter device of the present invention, the needle member includes a needle aperture so that the body fluid can flow through that needle aperture when the needle member is inserted into the body fluid-carrying conduit.

BRIEF DESCRIPTION OF THE DRAWINGS

The present invention may be more fully appreciated by referring to the drawings, wherein.

DETAILED DESCRIPTION

The overall nature of the present invention can be more fully appreciated and understood with reference to the following detailed description thereof, which refers to the drawings herein, and in which like numerals refer to like portions thereof.

It is initially noted, however, that while the following discussion is specifically directed to the use of the device of the present invention in connection with a catheter for use with dialysis equipment, that the overall nature of the present invention is not limited to that specific mode of utilization. It will thus be appreciated by those of ordinary skill in this art that the illustrative discussion which follows, and which relates to use in dialysis, is not so limiting, and that the overall nature of the present invention makes it adaptable for other such uses in connection with the necessary placement and stabilization of catheters, needles, cannulas and the like.

Figure 1:
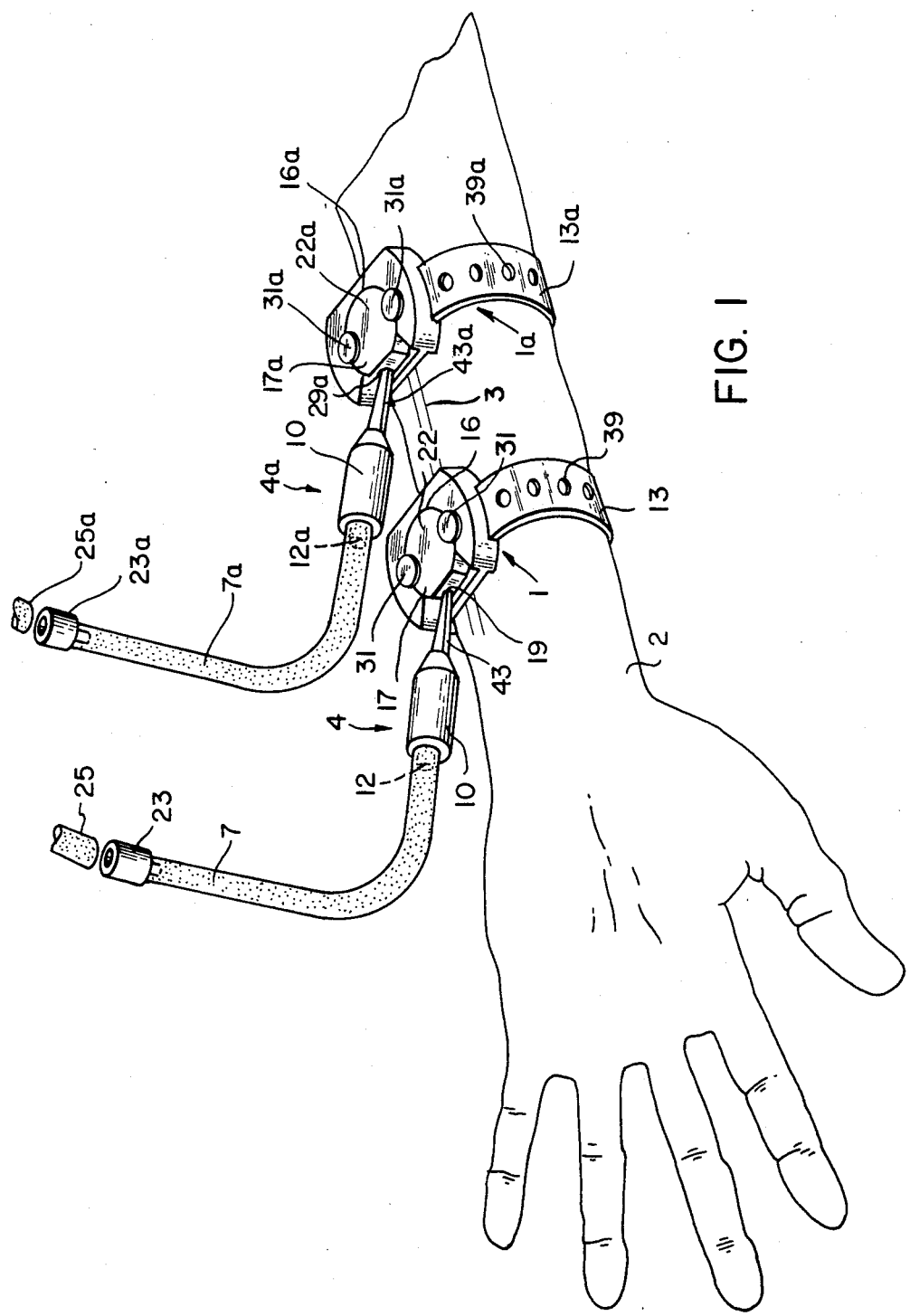
FIG. 1 is a top, elevational, perspective view of two devices in accordance with the present invention affixed to a patient.

Referring specifically to FIG. 1, a pair of the devices or "bracelets" of the present invention are shown as they would be used in connection with dialysis treatment of a patient. In particular, in this case the patient's arm 2 includes a previously imbedded graft 3 which has been subcutaneously applied to the dialysis patient's circulatory system in a previous surgical procedure. During dialysis treatment it is necessary to apply two catheters, a first catheter for removal of the impure blood from the patient and for the feeding of that impure blood to the dialysis equipment (not shown), and a second catheter for return of the then-purified blood back from the dialysis unit or equipment to the patient. In the case of FIG. 1, the first such device is the one designated 1, and the second such device, which accepts blood returned from the dialysis unit for entry back into the patient's circulatory system, is the device designated 1a, and is the device which is further up the patient's arm. The first device 1 can be referred to as the arterial device and the second or return device 1a can be referred to as the venus device.

In any event, the two devices 1 and 1a are shown in operable condition, with the catheters properly inserted into the graft 3. In this regard, the reference numerals followed by "a" are employed to designate portions of device 1a which correspond to the same portions of device 1, and the discussion which follows can thus relate to either such device. In each case, the catheters 4, 4a shown projecting into the graft 3, are thus secured and mounted on the devices 1 and 1a, respectively. The catheters 4, 4a include extending needle portions 5, 5a which are affixed to tubular conduits 7, 7a by means of plastic members 9, 9a. Insertion of the catheter into the bracelet device will be discussed in more detail below, but suffice it to say at this point that in FIG. 1 the devices are shown subsequent to such insertion.

In addition, each of the small lengths of tubular conduit 7, 7a is then available for connection to longer lengths of tubing 25, 25a by means of cylindrical connectors 23, 23a. Again, all of this is irrespective of the direction of blood flow in the device itself.

It is further noted that both of the catheters shown in FIG. 1 are disposed angularly with respect to the graft 3. In particular, they are shown at an acute or slight angle with respect thereto. This is a preferred embodiment of this invention. It has thus been realized that this form of catheter insertion is superior to, for example, a perpendicular needle insertion. In that latter case, the needle itself tends to oppose the flow of blood, causing undue pressure or blood disturbances. By using the device hereof, however, at the preferred angles, the needle does not oppose the blood flow and such disturbances are not created. In a particularly preferred embodiment an optimum angular placement of about 15° is employed.

Figure 2:
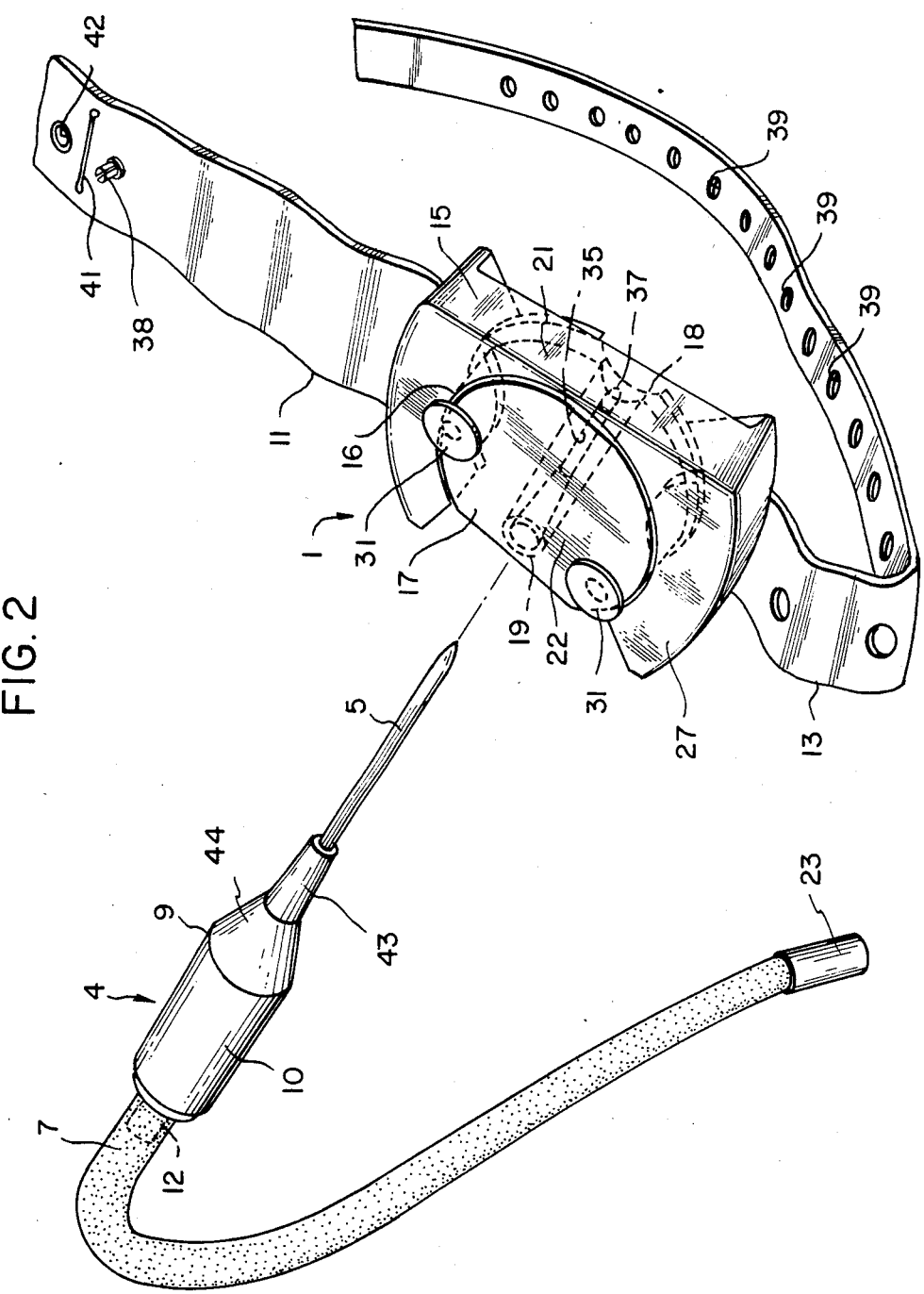
FIG. 2 is an elevational, perspective view of a device in accordance with the present invention in conjunction with a catheter, shown in an enlarged perspective view, prior to its insertion.

The devices 1 and 1a, which can be more clearly seen in FIG. 2, each includes a central anchoring portion 15, 15a as well as two extending arms 11, 11a and 13, 13a which are loose and very flexible, so that they can be applied to a patient's wrist or arm much like that of a wrist watch. However, for application to various other parts of the body, different lengths of flexible material, such as plastic, could be utilized.

Figure 3:
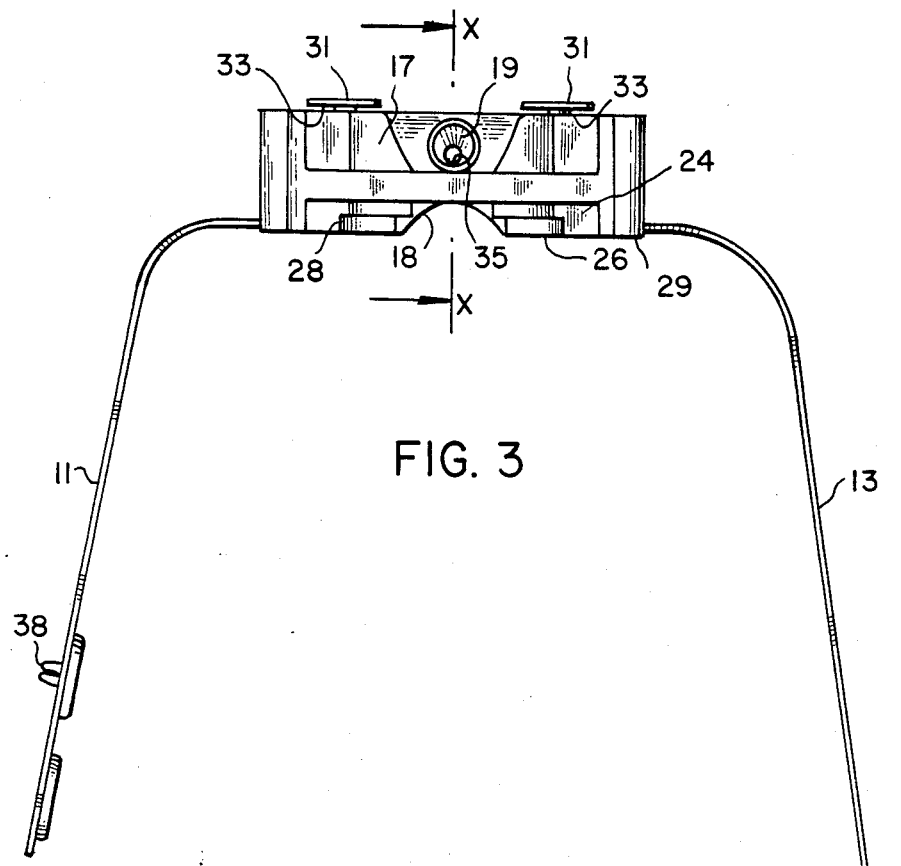
FIG. 3 is a side, elevational, perspective view of the device shown in FIG. 2.

Within the central anchoring portions 15, 15a, there are provided central aperture 16, 16a. Within these apertures 16, 16a are located adjustable or rotatable saddles 17, 17a which can best be seen in FIG. 3. The saddles 17, 17a are preferably separate elements which can be inserted into the apertures 16, 16a in the central anchoring portions 15, 15a of the devices 1, 1a. The rotatable saddles 17, 17a are substantially flat, cylinders, whose outer walls 21, 21a correspond with the shape of the central apertures 16, 16a in the anchoring portions 15, 15a. This permits the saddles 17, 17ato freely rotate within these central apertures 16, 16a. Furthermore, the upper surface 22, 22a of the rotatable saddles 17, 17a are substantially planar, and when the saddles 17, 17a are contained in the central apertures 16, 16a, these upper surfaces 22, 22a are coincident and in a common plane with the upper surfaces 27, 27a of the anchoring portions 15, 15a. Similarly, the lower surfaces 26, 26a of the rotatable saddles 17, 17a are also substantially planar, and thus when the saddles 17, 17a are contained within the central aperture 16, 16a, these lower surfaces 26, 26a are also preferably coincident and in a common plane with the lower surface 29, 29a of the anchoring portions 15, 15a. The rotation of the rotatable saddle 17, 17a within the central aperture 16, 16a will thus be about its central axis X as shown in FIG. 3, and when the device has been applied to a patient this axis X will be substantially perpendicular to the patient's skin. Thus, even after application of the device to the patient, but prior to insertion of the catheter itself, further fine alignment between the rotatable saddle 17, 17a and the graft 3 can be effected by rotation of the saddle 17, 17a about axis X, even by a small degree.

Mating of the saddle 17, 17a with the graft 3 is accomplished between the generally cylindrical shape of the graft 3 carrying blood therein, and the corresponding arcuate lower surface 18, 18a extending longitudinally along the bottom surface of the rotatable saddle 17, 17a.

The outer, cylindrical wall portion 21, 21a of rotatable saddle 17, 17a also includes an outwardly extending circumferential flange portion 28 at the lower end thereof, corresponding to the lower surface 26 also includes a corresponding circumferential groove 24 so that upon insertion of the rotatable saddle 17 into the central aperture 16, the circumferential flange 28 fits firmly into the groove 24, and thus prevents the rotatable saddle 17 from being removed upwardly from the central aperture 16 of the central anchoring portion 15. In this manner, when the saddle 17 is inserted into aperture 16, the circumferential flange 28 will be retained within the corresponding groove 24 when the saddle is at the proper location, so as to prevent accidental removal of the saddle 17 in an upward direction, as shown in FIG. 3. The flange 28 may be either a series of projecting flange portions, but preferably will constitute a continuous flange around the perimeter of the rotatable saddle.

In order to prevent removal of the rotatable saddle 17 from the central aperture 16 in a downward direction (as seen in FIG. 3) a pair of circular tabs 31 are mounted adjacent to the upper surfaces 22 and 27 of the rotatable saddle 17 and the anchoring portion 15, respectively. As shown in FIGS. 2 and 3, these circular tabs are mounted on posts 33 which, in turn, are mounted on the upper surface 22 of the rotatable saddle 17. Most importantly, however, they are located adjacent to the central aperture 16, and in a manner so that the surfaces of the circular tabs 31 extend over a portion of both the upper surfaces 22 and 27 of the rotatable saddle 17 and the anchoring portion 15. In this manner, the rotatable saddle 17 cannot be removed downwardly (i.e. in the direction of the lower surfaces 26 and 29 of the rotatable saddle 17 and the anchoring portion 15, respectively). It will thus be appreciated by those of ordinary skill in the art that these posts 33 could also have been mounted on the upper surface 27 of the anchoring portion 15, so long as the surface of the circular tabs 31 still overlaps both of the upper surfaces 22 and 27.

It will be appreciated that in this case, however, the relationship between the circumferential flange 23 and the corresponding groove 24 would have to be reversed so as to prevent downward removal of the rotatable saddle 17 from the position shown at FIG. 3. Thus, in that case the lower surface 29 of the anchoring portion 15 will include an inwardly extending circumferential flange portion, while the lower surface 26 of the rotatable saddle 17 will include a corresponding circumferential groove into which that flange will fit. In this manner, the cooperative effect of both these circular tabs 31 and the circular flange 28 prevent removal of the rotatable saddle 17 in either direction, and it is now permanently retained in the proper location within the central aperture 16.

Figure 4:
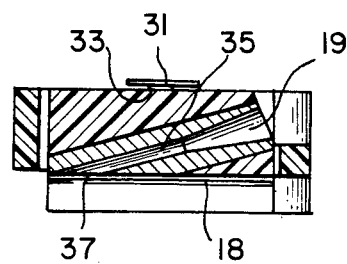
FIG. 4 is a side, elevational, perspective view of a rotatable saddle for use in connection with the device of the present invention.
Figure 5:
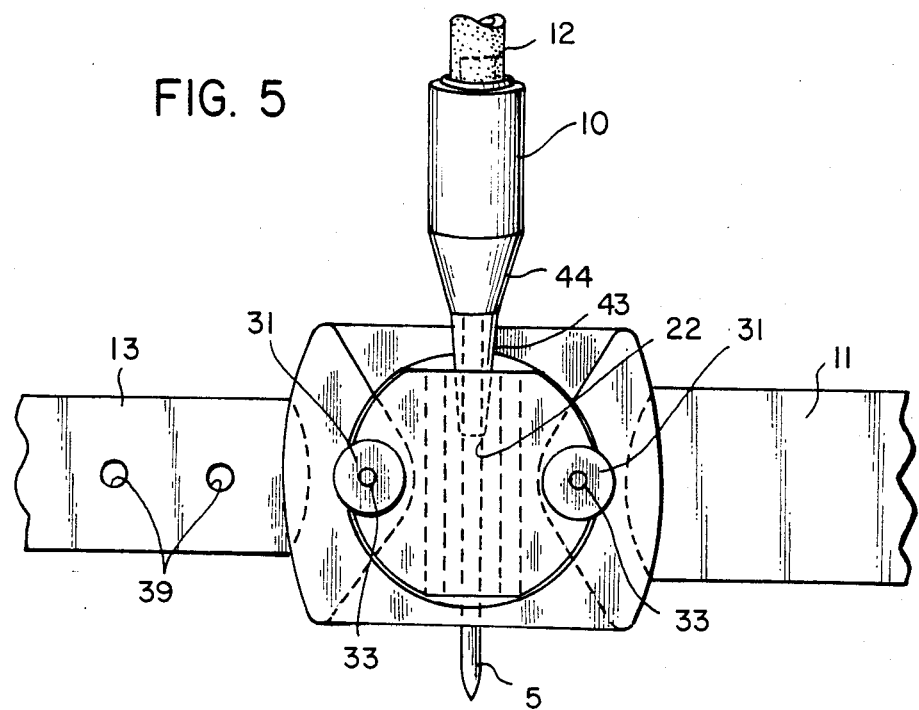
FIG. 5 is a top, elevational, perspective view of the catheter device in accordance with the present invention.
Figure 6:
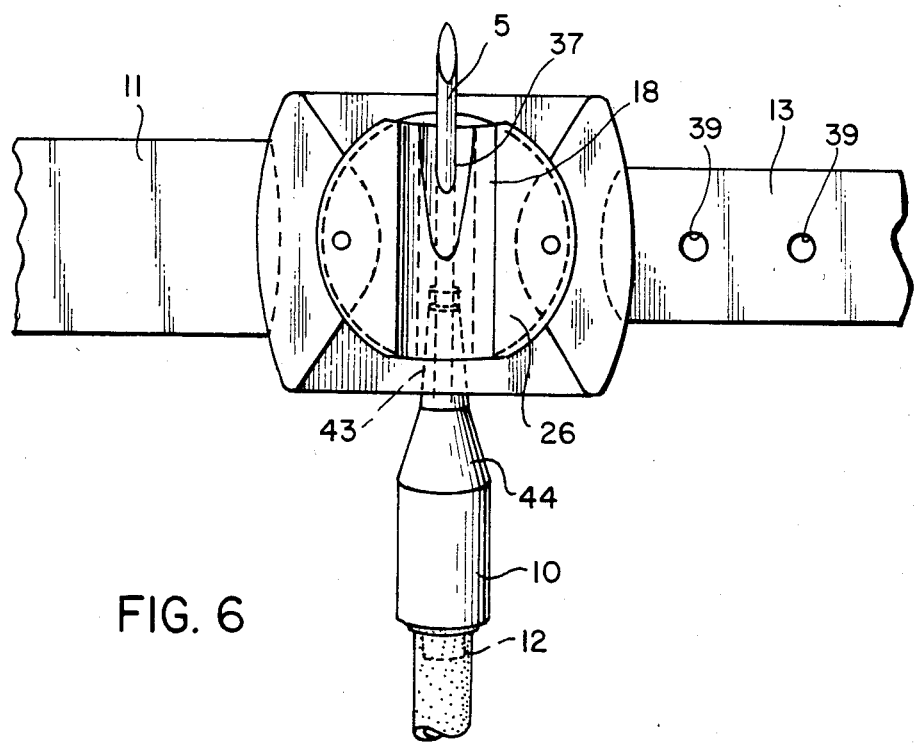
FIG. 6 is a bottom, elevational, perspective view of the catheter device shown in FIG. 5.

The rotatable saddle 17 includes an aperture 19 at a central location thereon, as can best be seen in FIGS. 3 and 4. This aperture 19 extends into a saddle channel 35 (see FIG. 4) extending through the saddle 17. Saddle channel 35 then terminates in an opening 37 in the arcuate portion 18 of the lower surface 26 of the rotatable saddle 17. In this manner, the catheter needle 5 can be inserted into the aperture 19, and thus into the saddle channel 35, so that the tip of the needle 5 ultimately extends through opening 37 for a predetermined distance, as can best be seen in FIGS. 5 and 6. That predetermined distance is such that the tip of the needle 5 will then be located at a preselected position, and most preferably substantially in the center of the graft 3 after insertion of the catheter. Furthermore, since the tip of the needle will be passing through saddle channel 35, it is important that the tip not contact the channel surface and remove or dislodge any small pieces of plastic or like material therefrom, since those pieces might then find their way into the patient's bloodstream. This can be accomplished in a number of ways. Firstly, if the relationship between the needle and saddle channel 35 is made precise enough, the needle will be precisely guided so as not to contact the saddle channel walls. Secondly, if the saddle itself is properly injection molded from appropriate plastic material, that plastic can be sufficiently hard and smooth so as to substantially eliminate the potential problem. Thirdly, in one embodiment it would also be possible to utilize a metallic insert so that the walls of the saddle channel 35 are made of metal and thereby also eliminate this potential problem.

The correct amount of penetration and stabilization of the catheter into the saddle 17 is further determined by the relationship between aperture 19 and the catheter 4 itself. As can best be seen in FIG. 2, the catheter 4 includes connector 9 for connecting the tubular conduit 7 to the needle 5. The connector 9 is preferably prepared from a relatively rigid material, such as plastic, and includes a central, cylindrical portion 10, and an extending portion 12 which has a reduced diameter. In this manner, the conduit 7, which is composed of PVC, having a much less rigid structure than connector 9, can be sealably affixed to the connector 9 by being slid over the extending portion 12 in the manner shown. A small amount of epoxy or other such adhesive can be applied to the outer surface extending portion 12 prior to application of the conduit 7 if desired, in order to solidify the bond therebetween. The other end of the cylindrical portion 10 includes tapered portion 44, which terminates at an end tapered portion 43, which is more gradually tapered than the tapered portion 44, and which includes an aperture for snuggly fitting about the needle 5 inserted therein. The conical or tapered shape of the end tapered portion 43 is adapted to mate with the corresponding conical or tapered shape of the end of the saddle channel 35 adjacent to the aperture 19 in the saddle 17, as can be seen in FIGS. 2 and 4, for firmly holding the catheter 4 in its desired position and depth, and for preventing premature removal or undesired movement thereof.

The following discussion concerns application of the bracelet device itself to the patient's arm 2, or to some other portion of the patient's anatomy. In the embodiment shown in FIG. 2 securing and locking of the device of this invention is facilitated by means of extending, flexible arms 11 and 13. These flexible arms are affixed to the central anchoring portion 15, such as by gluing, etc. The flexible arms 11 and 13 themselves can then be wrapped around the appropriate portion of a patient's anatomy, such as the arm. These flexible arms 11 and 13 can also then be affixed to each other, such as by means of a series of apertures 39 contained along arm 13, and one or more projecting members 38 contained on arm 11, along with a corresponding slot 41 extending through the arm 11 at a location adjacent to the projecting member 38, so that the flexible arm 13 can be inserted through slot 41, and affixed at the appropriate location corresponding to the size of the patient's arm or the like by means of insertion of projecting member 38 into the appropriate aperture 39 along flexible arm 13. Furthermore, since the projecting member 38 has a slotted or two-piece construction, with an expanded head portion, it can be "locked" in place by means of folding rigid aperture 42 over the top of projecting member 38 after stop 13 has been properly placed thereon, and snapping aperture 42 thereonto. One of ordinary skill in this art would, however, devise other means for locking arms 11 and 13 together, such as by the use of Velcro portions thereon, for example, or the like.

It will be understood that the embodiment described herein is merely exemplary and that a person skilled in the art may make many variations and modifications without departing from the spirit and scope of the invention. All such modifications and variations are intended to be included within the scope of the invention as defined in the appended claims.

I claim:

1. A device for mounting a catheter in a body fluid-carrying conduit in a patient and securing the catheter to said patient comprising anchoring means for attachment to said patient at a predetermined location on said patient at which said body fluid-carrying conduit is located, said anchoring means including an upper surface and an aperture therein, a rotatable saddle rotatably mounted in said aperture in said anchoring means, said rotatable saddle rotatable about an axis substantially perpendicular to said predetermined location on said patient and including an for receiving said catheter, said rotatable saddle further including a contact surface for contacting said body fluid-carrying conduit in said patient and a saddle channel extending between said aperture and said contact surface, and stabilizing means affixed to said rotatable saddle for preventing removal of said rotatable saddle from said anchoring means, without interfering with said rotation of said rotatable saddle, said stabilizing means including at least one stabilizing member located in a plane adjacent to and overlapping said upper surface of said anchoring means whereby said device can be attached to said patient at said predetermined location and subsequently adjusted by rotating said rotatable saddle so as to align said saddle channel with said predetermined location on said patient, and said catheter can be accurately located in said body fluid-carrying conduit when it has been inserted through said saddle channel.

2. The device of claim 1, wherein said anchoring means comprises a central portion and a pair of arm portions extending from opposite sides of said central portion, said arm portions being affixable to said patient at said predetermined location.

3. The device of claim 2, wherein said arm portions comprise flexible strap means.

4. The device of claim 1, wherein said rotatable saddle includes an upper surface, both of said upper surfaces of said anchoring means and said rotatable saddle being disposed in a common plane, and wherein said stabilizing means is located in a plane adjacent to said common plane and overlapping said upper surfaces of both said rotatable saddle and said anchoring means.

5. The device of claim 4, wherein said stabilizing means includes an outwardly extending flange portion of said rotatable saddle, and wherein said aperture includes a groove portion for retaining said flange portion of said rotatable saddle when said rotatable saddle is contained within said aperture.

6. The device of claim 1, including a plurality of said stabilizing members.

7. The device of claim 1, wherein said at least one stabilizing member is mounted on the upper surface of said rotatable saddle.

8. The device of claim 1, wherein said at least one stabilizing member is substantially circular.

9. The device of claim 1, wherein said saddle channel includes a surface which is sufficiently hard so as to prevent penetration by said catheter as said catheter is being inserted thereinto.

10. The device of claim 9, wherein said surface of said saddle channel comprises a metallic surface.

11. The device of claim 3, including locking means for locking said anchoring means to said patient.

12. The device of claim 11, wherein said locking means comprises a male locking member associated with one of said flexible strap means and a female locking member associated with the other of said flexible strap means.

13. The device of claim 1, wherein said saddle channel in said adjustable saddle includes stop means for limiting the depth to which said catheter may be inserted into said saddle channel.

14. The device of claim 13, wherein said stop means has a conical configuration adapted to mate with the shape of said catheter so as to stabilize said catheter after it has been inserted into said saddle channel.

15. A catheter device for being affixed to a patient at the location of a body fluid-carrying conduit in said patient comprising a catheter including a needle member and tubular catheter conduit means for supplying fluid to or removing fluid from said needle member, anchoring means for attachment to said patient at a predetermined location on said patient at which said body fluid-carrying conduit is located, said anchoring means including an upper surface and an aperture therein, a rotatable saddle rotatably mounted in said aperture in said anchoring means, said rotatable saddle including an aperture for receiving said catheter, said rotatable saddle further including a contact surface for contacting said body fluid-carrying conduit in said patient and a saddle channel extending between said aperture and said contact surface, and stabilizing means affixed to said rotatable saddle for preventing removal of said rotatable saddle from said anchoring means without interfering with said rotation of said rotatable saddle, said stabilizing means including at least one stabilizing member located in a plane adjacent to and overlapping said upper surface of said anchoring means whereby said device can be attached to said patient at said predetermined location and subsequently adjusted by rotating said rotatable saddle so as to align said saddle channel with said predetermined location on said patient, and said catheter can be accurately located in said body fluid-carrying conduit when it has been inserted into said aperture.

16. The catheter device of claim 15, wherein said saddle channel in said rotatable saddle includes stop means for limiting the depth to which said catheter may be inserted into said saddle channel.

17. The catheter device of claim 16, wherein said tubular catheter conduit means and said saddle channel in said rotatable saddle have corresponding shapes whereby said catheter is stabilized after it has been inserted into said saddle channel.

18. The catheter device of claim 15, wherein said rotatable saddle includes an upper surface, both of said upper surfaces of said rotatable saddle and said anchoring means being disposed in a common plane, and wherein said stabilizing means is located in a plane adjacent to said common plane and overlapping said upper surfaces of said rotatable saddle and said anchoring means.

19. The catheter device of claim 15, including a plurality of said stabilizing members.

20. The catheter device of claim 15, wherein said at least one stabilizing member is mounted on the upper surface of said rotatable saddle.

21. The catheter device of claim 15, wherein said at least one stabilizing member is substantially circular.

22. The catheter device of claim 15, wherein said stabilizing means includes an outwardly extending flange portion of said rotatable saddle, and wherein said central aperture includes a groove portion for retaining said flange portion of said rotatable saddle when said rotatable saddle is contained within said central aperture.

23. The catheter device of claim 15, wherein said saddle channel includes a surface which is sufficiently hard so as to prevent penetration by said catheter thereinto.

24. The catheter device of claim 23, wherein said surface of said saddle channel comprises a metallic surface.

25. The catheter device of claim 15, wherein said needle member includes a needle aperture whereby said body fluid can flow through said needle aperture when said needle member is inserted into said body fluid-carrying conduit.

26. The catheter device of claim 15, wherein said anchoring means comprises a central portion and a pair of arm portions extending from opposite sides of said central portion, said arm portions being adapted to be affixed to said patient at said predetermined location.

27. The catheter device of claim 26, wherein said arm portions comprise flexible strap means.

28. A device for mounting a catheter in a body fluid-carrying conduit in a patient and securing the catheter to said patient comprising anchoring means for attachment to said patient at a predetermined location on said patient at which said body fluid-carrying conduit is located, said anchoring means including an upper surface and an aperture therein, a rotatable saddle rotatably mounted in said aperture in said anchoring means, said rotatable saddle rotatable about an axis substantially perpendicular to said predetermined location on said patient and including an aperture for receiving said catheter, said rotatable saddle further including a contact surface for contacting said body fluid-carrying conduit in said patient and a saddle channel extending between said aperture and said contact surface, and stabilizing means affixed to said anchoring means for preventing removal of said rotatable saddle from said anchoring means, without interfering with said rotation of said rotatable saddle, said stabilizing means including at least one stabilizing member located in a plane adjacent to and overlapping said upper surface of said anchoring means whereby said device can be attached to said patient at said predetermined location and subsequently adjusted by rotating said rotatable saddle so as to align said saddle channel with said predetermined location on said patient, and said catheter can be accurately located in said body fluid-carrying conduit when it has been inserted through said saddle channel.

29. The device of claim 28, wherein said anchoring means comprises a central portion and a pair of arm portions extending from opposite sides of said central portion, said arm portions being affixable to said patient at said predetermined location.

30. The device of claim 29, wherein said arm portions comprise flexible strap means.

31. The device of claim 28, wherein said rotatable saddle includes an upper surface, and said anchoring means includes an upper surface, both of said upper surfaces being disposed in a common plane, and wherein said stabilizing means comprises at least one stabilizing member mounted in a plane adjacent to said common plane and overlapping said upper surfaces of both said rotatable saddle and said anchoring means so as to retain said rotatable saddle in said central aperture.

32. The device of claim 31, wherein said stabilizing means includes an outwardly extending flange portion of said rotatable saddle, and wherein said aperture includes a groove portion for retaining said flange portion of said rotatable saddle when said rotatable saddle is contained within said aperture.

33. The device of claim 31, including a plurality of said stabilizing members.

34. The device of claim 31, wherein said at least one stabilizing member is substantially circular.

35. The device of claim 28, wherein said saddle channel includes a surface which is sufficiently hard so as to prevent penetration by said catheter as said catheter is being inserted thereinto.

36. The device of claim 34, wherein said surface of said channel comprises a metallic surface.

37. The device of claim 30, including locking means for locking said anchoring means to said patient.

38. The device of claim 37, wherein said locking means comprises a male locking member associated with one of said flexible strap means and a female locking member associated with the other of said flexible strap means.

39. The device of claim 28, wherein said saddle channel in said adjustable saddle includes stop means for limiting the depth to which said catheter may be inserted into said channel.

40. The device of claim 39, wherein said stop means has a conical configuration adapted to mate with the shape of said catheter so as to stabilize said catheter after it has been inserted into said saddle channel.

* * * * *

UNITED STATES PATENT AND TRADEMARK OFFICE
CERTIFICATE OF CORRECTION

PATENT NO. : 4,666,434
DATED : May 19, 1987
INVENTOR(S) : Jerry M. Kaufman

It is certified that error appears in the above-indentified patent and that said Letters Patent is hereby corrected as shown below:

Column 8, line 34, after "an" insert --aperture--.

Signed and Sealed this

Sixth Day of August, 1996

Attest:

BRUCE LEHMAN

Attesting Officer    Commissioner of Patents and Trademarks